(12) United States Patent
Bentley et al.

(10) Patent No.: US 9,040,060 B2
(45) Date of Patent: May 26, 2015

(54) HYDROLYTICALLY DEGRADABLE ALKYLENE OXIDE BASED POLYMERS

(75) Inventors: Michael D. Bentley, Huntsville, AL (US); J. Milton Harris, Huntsville, AL (US); Xuan Zhao, Beijing (CN); William Dudley Battle, III, Huntsville, AL (US); Xiaoming Shen, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 366 days.

(21) Appl. No.: 13/108,616

(22) Filed: May 16, 2011

(65) Prior Publication Data

US 2011/0217343 A1  Sep. 8, 2011

Related U.S. Application Data

(63) Continuation of application No. 10/371,996, filed on Feb. 14, 2003.

(60) Provisional application No. 60/357,350, filed on Feb. 15, 2002.

(51) Int. Cl.
*A61K 9/00* (2006.01)
*A61K 47/32* (2006.01)
*C08G 65/04* (2006.01)
*A61K 47/34* (2006.01)
*C08G 64/18* (2006.01)
*C08G 65/329* (2006.01)
*C08G 65/333* (2006.01)
*A61K 9/06* (2006.01)

(52) U.S. Cl.
CPC . *C08G 65/04* (2013.01); *A61K 9/00* (2013.01); *A61K 9/06* (2013.01); *A61K 47/34* (2013.01); *C08G 64/183* (2013.01); *C08G 65/329* (2013.01); *C08G 65/333* (2013.01); *C08G 65/33337* (2013.01); *C08G 65/33344* (2013.01); *C08G 65/33396* (2013.01); *C08L 2203/02* (2013.01)

(58) Field of Classification Search
CPC ........... A61K 9/00; A61K 47/32; A61K 9/06; C08G 65/33396
USPC ......................................................... 424/400
See application file for complete search history.

(56) References Cited

U.S. PATENT DOCUMENTS

| | | | |
|---|---|---|---|
| 3,227,740 A * | 1/1966 | Fenton | 558/266 |
| 4,072,704 A * | 2/1978 | Langdon | 558/266 |
| 4,189,609 A * | 2/1980 | Langdon | 568/601 |
| 4,866,143 A | 9/1989 | Gagnon et al. | |
| 5,330,768 A | 7/1994 | Park et al. | |
| 5,650,234 A | 7/1997 | Dolence et al. | |
| 5,861,174 A | 1/1999 | Stratton et al. | |
| 6,083,524 A * | 7/2000 | Sawhney et al. | 424/426 |
| 6,177,095 B1 | 1/2001 | Sawhney et al. | |
| 6,201,065 B1 | 3/2001 | Pathak et al. | |
| 6,258,351 B1 | 7/2001 | Harris | |
| 6,348,558 B1 | 2/2002 | Harris et al. | |
| 7,074,878 B1 | 7/2006 | Harris et al. | |
| 2003/0023023 A1 | 1/2003 | Harris et al. | |
| 2004/0072799 A1 * | 4/2004 | Li et al. | 514/58 |
| 2006/0239961 A1 | 10/2006 | Bentley et al. | |

FOREIGN PATENT DOCUMENTS

| | | |
|---|---|---|
| EP | 0 258 780 | 3/1988 |
| WO | 2003/070805 | 8/2003 |

OTHER PUBLICATIONS

Anh, et al., "Slow eroding biodegradable multiblock poloxamer copolymers", 54 Polymer International 842, Wiley, (2005).
Cohn, et al., "Tailoring Novel Temperature-Responsive Polymers", Sixth World Biomaterials Congress Transactions, pp. 643, (2000).
Huang, et al., "Synthesis and Characterization of . . . ", Polymer Preprints, vol. 42, No. 2, pp. 147-148, (2001).
Ruel-Gariepy, et al., "In Situ-Forming Hydrogels—Review of Temperature-Sensitive Systems", European Journal of Pharmaceutics and Biopharmaceutics, vol. 58, pp. 409-426, (2004).
Takahashi, et al., "Thermoreversable Gelation and Phase Separation in Aqueous Methyl Cellulose Solutions", 39 Journal of Polymer Science B: Polymer Physics 91, Wiley, (2000).
Zhao, et al., "Synthesizing Oligomers of Poloxamer 407 as Degradable Thermal-Sensitive Depot Materials for Sustained Drug Release", 30th Annual Meeting and Exposition of the Controlled Release Society, Glasgow, Scotland, (Jul. 19-23, 2003).
International Search Report, mailed Jul. 3, 2003, corresponding to PCT Application No. PCT/US03/05113, as published in WO 03/070805 on Aug. 28, 2003.
Written Opinion, mailed Oct. 27, 2003, corresponding to PCT Application No. PCT/US03/05113.
International Preliminary Examination Report, mailed Jan. 7, 2004, corresponding to PCT/US03/05113.
European Office Action dated Feb. 24, 2006, corresponding to European Application No. 03 709 198.0-2102.
European Office Action dated Mar. 2, 2007, corresponding to European Application No. 03 709 198.00-2102.

(Continued)

*Primary Examiner* — Michael G Hartley
*Assistant Examiner* — Lance Rider
(74) *Attorney, Agent, or Firm* — Susan T. Evans; Mark A. Wilson

(57) ABSTRACT

The present invention provides a water soluble, non-peptidic polymer comprising two or more alkylene oxide-based oligomers linked together by hydrolytically degradable linkages such as carbonates. Typically, the oligomer portion of the polymer is an amphiphilic triblock copolymer having a central propylene oxide block or butylene oxide block positioned between two ethylene oxide blocks. The polymer can be hydrolytically degraded into oligomers under physiological conditions. In aqueous media, the polymer preferably forms thermally reversible, hydrolytically degradable hydrogels that can be used, for example, for drug delivery and related biomedical applications.

12 Claims, 3 Drawing Sheets

(56) References Cited

OTHER PUBLICATIONS

NEKTAR™—Transforming Therapeutics, Nektar Molecule Engineering: Polyethylene Glycol and Derivatives for Advanced PEGylation, 24 pages, Catalog—2003, (Jul. 2003).

NOF Corporation, PEG Derivatives, Phospholipid and Drug Delivery Materials for Pharmaceuticals, pp. 1-46, Catalogue 2003-1st, (Jan. 2003).

NOF Corporation, PEG Derivatives, Phospholipid and Drug Delivery Materials for Pharmaceuticals, pp. 1-50, Catalogue 2003-2nd, (Mar. 2004).

Shearwater Polymers, Inc., Polyethylene Glycol and Derivatives, 50 pages, (Catalog—Mar. 1995).

Shearwater Polymers, Inc., Polyethylene Glycol and Derivatives, 55 pages, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—Jan. 2000).

Shearwater Corporation, Polyethylene Glycol and Derivatives for Biomedical Applications, 20 pages, (Catalog—Jul. 2001).

* cited by examiner

Figure 1. Phase diagram of oligomers of poloxamer 407
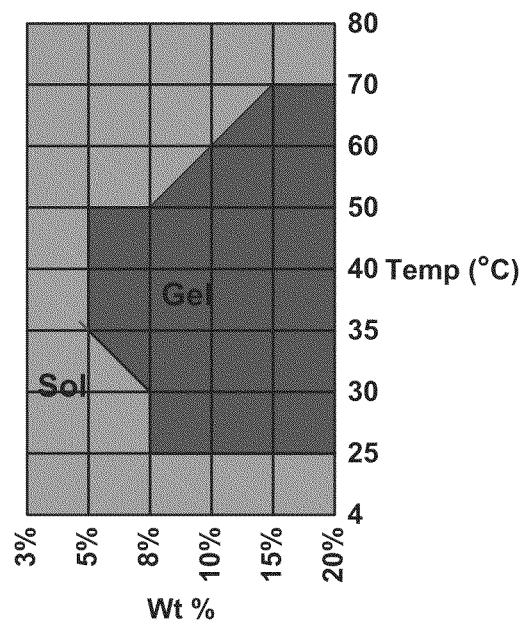
Figure 2. Dissolution study of the gels formed by degradable oligomers in buffer (pH 7)
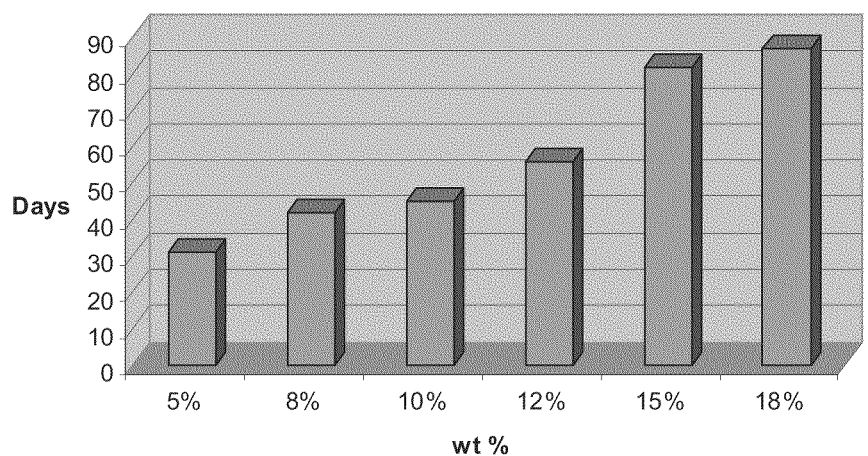

Figure 3
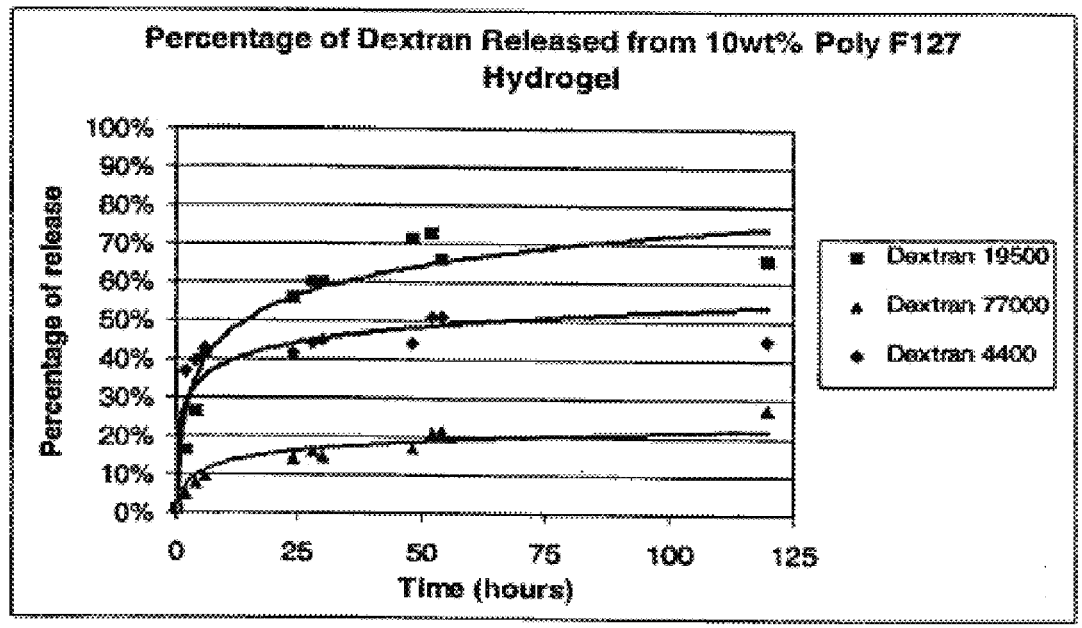
Figure 4. Release of Biphalin and PEG-Biphalin from the degradable hydrogel (12 wt% oligomer)
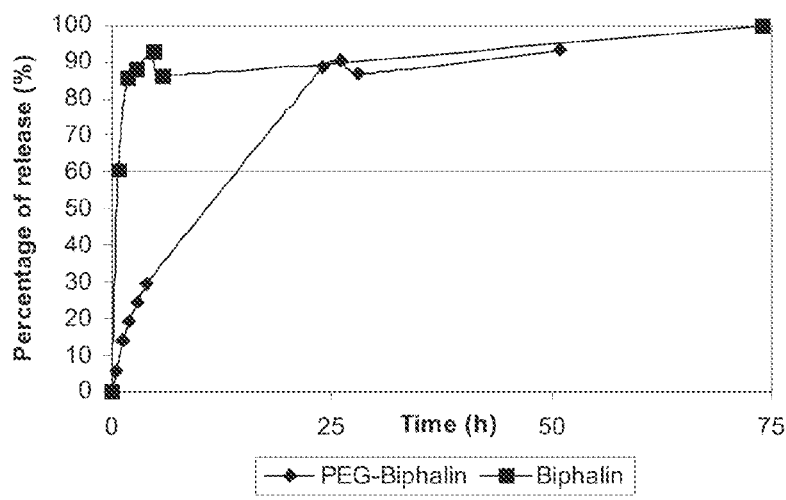

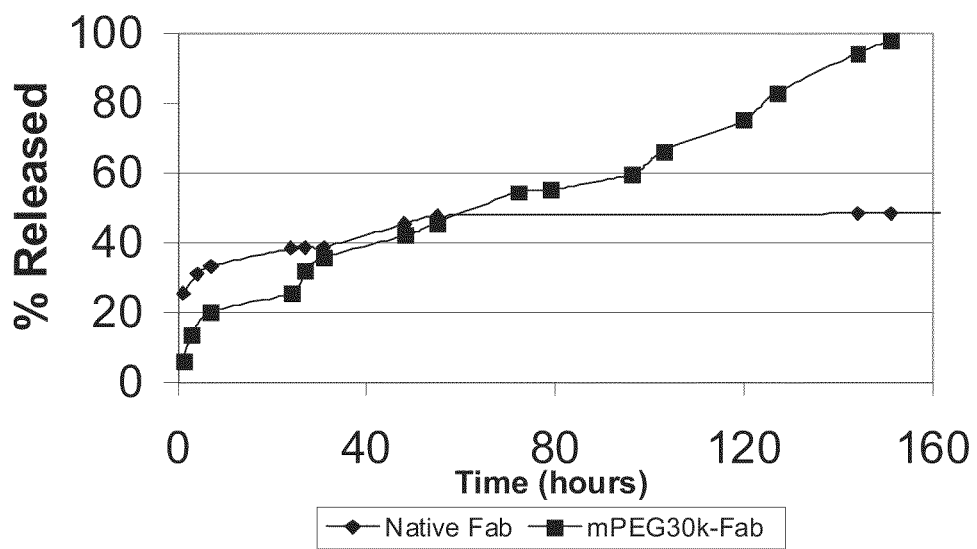
Figure 5. Release profile of Fab and mono-PEGylated Fab from degradable thermal-sensitive gel (9 wt%)

HYDROLYTICALLY DEGRADABLE ALKYLENE OXIDE BASED POLYMERS

This application is a continuation of U.S. patent application Ser. No. 10/371,996, filed Feb. 14, 2003, which claims the benefit of priority of U.S. Provisional Patent Application No. 60/357,350, filed Feb. 15, 2002, the contents of which are incorporated herein by reference in their entireties.

FIELD

The present invention generally relates to water soluble, hydrolytically degradable, and nonpeptidic polymers. More specifically, the invention is directed to hydrolytically degradable polymers comprising oligomers of particular alkylene oxide triblock copolymers, and to compositions and uses thereof. The polymers are suitable for drug enhancement, in vivo delivery of biologically active agents, and use in medical devices.

BACKGROUND

The hydrophilic polymer poly(ethylene glycol), abbreviated "PEG", is of considerable utility in biological applications and in medicine. PEG is a polymer that is soluble in water and in many organic solvents, is non-toxic, and non-immunogenic. In recent years, the use of PEG has expanded into the biomedical, biotechnical and pharmaceutical arenas to encompass a variety of applications. For instance, covalent attachment of PEG to therapeutic polypeptides has been employed to shield antigenic epitopes of the polypeptide to reduce reticuloendothelial clearance and proteolytic degradation of the polypeptide. PEG conjugation to therapeutically active polypeptides or small molecules can also be used to increase the circulating half-life, improve solubility, reduce renal filtration, or alter the biodistribution of a bioactive agent.

Another use of PEG is to form a crosslinked matrix or gel of PEG molecules which is substantially non-soluble, but swellable in water. PEG hydrogels, which are water-swollen gels, have been used for both wound covering and drug delivery. PEG hydrogels are typically prepared by incorporating the soluble, hydrophilic polymer into a chemically crosslinked network or matrix so that addition of water produces an insoluble, swollen gel. One application of such hydrogels involves the delivery of drugs. In one approach, a therapeutic agent for delivery from a hydrogel is not covalently attached to the PEGs forming the hydrogel, but rather is entrapped within the crosslinked hydrogel matrix and passes through interstices in the matrix upon release.

Many of the commonly employed methods for preparing hydrogels result in the incorporation of substantial non-PEG components into the hydrogel composition including crosslinking agents and catalysts, and/or require the use of radiation as a crosslinking initiator. See, for example, U.S. Pat. No. 4,894,238, which describes linear PEG incorporated into a crosslinked network by reaction with a triol and a diisocyanate to form hydrolytically-stable ("nondegradable") urethane linkages. Another similar approach for preparation of non-degradable PEG hydrogels has been demonstrated by Gayet and Fortier in J. Controlled Release, 38, 177-184 (1996), in which linear PEG was activated as the p-nitrophenylcarbonate and crosslinked by reaction with a protein, bovine serum albumin. Methods such as these result in gels containing non-PEG contaminants. As a result, degradation and dissolution of the matrix can result in undesirable or toxic components being released into the bloodstream. Further, the harsh gelling conditions employed in such methods can often inactivate or degrade drug substances incorporated in such hydrogel compositions.

Early implantable gel delivery systems, as disclosed in U.S. Pat. Nos. 4,938,763 and 5,278,202, were either thermoplastic or thermosetting. The thermoplastic systems involved the formation of polymeric solutions in solvents. Just prior to injection, a curing agent was added to the polymeric solution. After injection, the curing agent caused crosslinking of the polymeric materials and the polymeric solution was exposed to body fluids or water which diffused the solvent away from the polymer-drug mixture, allowing water to diffuse into the mixture. The loss of solvent caused the polymer-drug mixture to coagulate and encapsulate the drug within the polymeric gel. These early gel systems typically used organic solvents to hold the polymer and drug in solution. Organic solvents are often toxic and irritating to tissue.

More recent implantable gel delivery systems have been developed that can be prepared in aqueous solutions. These systems involve a class of block copolymers composed of polyethylene oxide and polypropylene oxide. The polymers are usually synthesized to produce an arrangement of a polypropylene oxide blocks sandwiched between two polyethylene oxide blocks. The polyethylene oxide is hydrophilic while the polypropylene oxide is hydrophobic. The polyethylene oxide and polypropylene oxide copolymers absorb water and form a gel when maintained at a sufficient concentration and heated above a critical temperature. A common polyethylene oxide-polypropylene oxide polymeric solution is known as Poloxamer, a version of which is marketed under the tradename Pluronic™ by the BASF Corporation of Mt. Olive, N.J.

The polyethylene oxide and polypropylene oxide gels are generally less toxic than previous gels that contained or were prepared from organic solvents. However, Poloxamer-based gels are not biodegradable, making drug release from such systems highly unpredictable. Moreover, certain poloxamer based gels have been unsuccessful in clinical trials, due not only to performance limitations, but also due to the adverse side effects attributed to the high concentrations of polymer that must be delivered in order to achieve gelation at body temperature.

In general, the development of hydrogel formulations for drug delivery has progressed rather slowly, partially due to the problems described above and additionally due to problems associated with parenteral administration of hydrogels.

Thus, there is a need for improved polymer and polymer compositions having low toxicity, biodegradability, and favorable release kinetics. Moreover, it would be advantageous if such polymer and polymer compositions could be readily synthesized and characterized, and additionally be used to form gels without the need for additional cross-linking agents, additional co-monomers, and the like. Lastly, it would be highly desirable to provide hydrogel formulations capable of administration by injection, e.g., as free flowing solutions, rather than requiring implantation.

The present invention is based upon the Applicant's preparation of a polymer that meets the above criteria.

SUMMARY

In one aspect, the present invention is directed to a water soluble, nonpeptidic polymer comprising two or more alkylene oxide-based oligomers linked together by hydrolytically degradable linkages such as carbonates. Typically, the oligomer portion of the polymer is an amphiphilic triblock copolymer having a central propylene oxide block or butylene oxide block positioned between two ethylene oxide blocks.

In preparing and characterizing the polymers of the invention, the Applicants discovered that aqueous solutions of the polymers of the invention exhibit a surprising property—they are responsive to changes in temperature (i.e., they are "thermally sensitive"). More particularly, aqueous solutions of the polymers of the invention form reverse thermal gels, that is to say, depending upon concentration, they exist as solutions at low temperatures, whilst forming hydrogels at body temperature. Moreover, the polymers form thermally-induced gels at extremely low concentrations.

A polymer of the invention may generally be represented as a polyether carbonate having the formula:

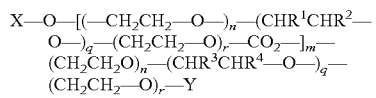

wherein:

n, q, and r are integers each independently ranging from about 2 to about 2,000, m is an integer ranging from 1 to about 2000, where $R^1$ is H when $R^2$ is alkyl or $R^1$ is alkyl when $R^2$ is H, $R^3$ is H when $R^4$ is alkyl or $R^3$ is alkyl when $R^4$ is H, and X and Y are each independently selected from the group consisting of H, alkyl, alkenyl, aryl, or a reactive moiety.

The value of m can range from 1 to about 2000, although m has a preferred range of about 1 to about 20. In a particular embodiment, the value of m ranges from about 1 to 5. The value of n is normally in the range of about 80 to about 120; q normally ranges from about 40 to about 70. Alkyl groups represented by $R^1$, $R^2$, $R^3$, or $R^4$ are typically H or lower alkyl, and when lower alkyl, are preferably either a methyl or an ethyl group.

Although in a preferred embodiment the polymer of the invention possesses carbonate linkages coupling the oligomer portions of the polymer, hydrolytically degradable linkages such as sulfite, thiourea, or thiocarbonate may also be employed.

In one particular embodiment, the polymer of the invention comprises a poly(ether carbonate) having the formula:

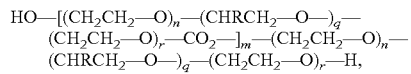

where the variables have the values described above.

The polymers of the invention, by virtue of their carbonate linkages, are hydrolytically degradable under mild conditions, and hydrolyze to produce soluble oligomer fragments of significantly lower molecular weight than the starting polymer.

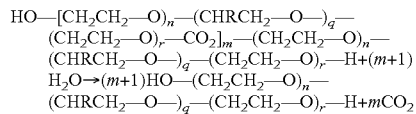

Thus, the polymers of the invention can readily degrade in the body to facilitate their removal. The degradation products are themselves normally nontoxic small PEGs that typically are rapidly cleared from the body.

The polymer can be prepared by a number of different synthetic approaches. According to another aspect of the invention, a poly(ether carbonate) is prepared by polymerizing or coupling an activated oligomer having the formula of:

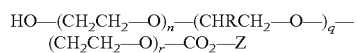

where n, q, r, and R are as defined above and Z is a reactive leaving group such as N-succinimidyl, 1-benzotriazolyl, or p-nitrophenyl.

More particularly, the polymer can be prepared by polymerizing or coupling co-polymeric oligomers of the formula:

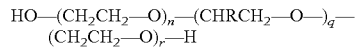

with an activating molecule of Z—O—CO$_2$—Z, where n, q, r, R, and Z are as described above.

Alternatively, the ethylene oxide oligomer

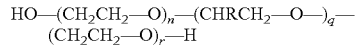

can be polymerized with a bifunctional alkylene oxide oligomer:

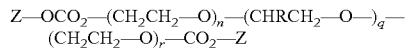

where n, q, r, and Z are as described above, to form the poly(ether carbonate).

The polymerization or coupling reactions are conducted either in an organic solvent or in a melt, in the presence of a base. Examples of suitable solvents include acetonitrile, THF, dimethylformamide, dimethylsulfoxide, benzene, toluene, the xylenes, chloroform, and methylene chloride. Examples of suitable organic bases include triethylamine, pyridine, quinoline, 4,4-dimethylaminopyridine and triethylamine. The polymerization reactions are typically conducted at a temperature of from about 37° C. to 100° C., typically from about 45° C. to 100° C., and advantageously from about 70° C. to 90° C.

Also provided is (i) a polymer activated for conjugation to a biologically active agent such as a protein or peptide, and (ii) the resulting polymer conjugate. The polymer can impart desirable characteristics to a given bioactive agent such as improved water solubility, reduced immunogenicity, and longer circulating half-life, although the reverse thermal gelation characteristics of the polymer itself may be lost.

In a particular embodiment, the polymer of this invention is modified at one terminus with alkyl or aryl groups to make one end of the polymer inert.

In yet another embodiment, the polymer can be activated at one or more of its termini to form a terminal reactive moiety. Thus, such a modified or activated poly(ether carbonate) of the invention is represented as:

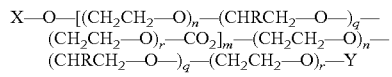

where m, n, q, r, and R are as defined above, and X and Y are independently selected from the group consisting of H, alkyl, alkenyl, aryl, or a reactive group. Reactive groups include but are not limited to acryloyl, tresyl, N-succinimidyloxycarbonyl, 1-benzotriazolyloxycarbonyl, p-nitrophenyloxycarbonyl, N-maleimidyl, aldehydes, acetals, 1-imidazolylcarbonyl, vinylsulfone, iodoacetamide, and o-pyridyldithiyl. Alternatively, X and Y can further include linker or spacer groups terminating in reactive groups such as aldehyde, ester, carboxylic acid, vinyl sulfone, succinimidyl propionate, succinimidyl butanoate, N-maleimidyl or —S—S-ortho-pyridyl. A wide variety of activating groups and linkers can be used.

Thus, this invention provides a versatile polymer that is especially suited for forming a thermally reversible hydrogel for sustained delivery of biologically active agents. The polymer is easy to prepare and can be synthesized in large quantities. The polymer can be formed in a single reaction with multiple degradable carbonate linkages in the backbone. The hydrogel of this invention can be degraded under physiological conditions to generate oligomers of predetermined molecular weight that can be easily cleared from the body.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

BRIEF DESCRIPTION OF THE DRAWINGS

Having thus described the invention in general terms, reference will now be made to the accompanying drawings, wherein:

FIG. 1 is a phase diagram indicating the reverse thermal gelation characteristics of an illustrative polymer of the invention in aqueous solution depending on temperature and concentration of the polymer as described in detail in Example 2;

FIG. 2 is a plot demonstrating the dissolution times for representative polymer gels having varying concentrations of polymer as described in detail in Example 3;

FIG. 3 shows the release profiles of three fluorescein isothiocyanate dextrans of differing molecular weights from an exemplary hydrogel composition of the invention under conditions simulating those of a mammalian body as described in detail in Example 4;

FIG. 4 demonstrates the release profiles over time of the model compounds, biphalin and pegylated biphalin, from an illustrative hydrogel of the invention as described in Example 5; and FIG. 5 shows the release profiles of a Fab fragment and its mono-pegylated counterpart from an exemplary hydrogel of the invention as described in detail in Example 6.

DETAILED DESCRIPTION

The invention will now be described more fully hereinafter with reference to the accompanying examples, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

The following terms as used herein have the meanings indicated. As used in the specification, and in the appended claims, the singular forms "a", "an", "the", include plural referents unless the context clearly dictates otherwise.

As used herein, the term "polymer" means a molecule formed by the chemical union of two or more oligomer units. The chemical units are normally linked together by covalent linkages. The two or more combining units in a polymer can be all the same, in which case the polymer is referred to as a homopolymer. The combining or subunits can also be different and, thus, the polymer will be a combination of the different units. These polymers are referred to as copolymers.

The term "oligomer" is used herein to mean a molecule, typically an organic molecule, which in itself is formed by the chemical union of two or more monomer units. The monomer units of an oligomer may be different or all the same. An oligomer is capable of reacting with another oligomer which is same or different, in a coupling reaction to form a polymer composed of oligomeric subunits. As used herein, the term oligomer by no means limits the size of the molecule or the number of combining units or monomers in the oligomer. Rather, "oligomer" is used to indicate a subunit for forming a polymer of the invention. The structure of an oligomer in the resulting polymer may be slightly different in chemical structure from the oligomer prior to polymerization due to the coupling reaction and the formation of covalent linkages.

The term "carbonate linkage" is used herein to mean a linkage that includes the group —O—$CO_2$—. It is to be understood that a carbonate linkage is distinct from a carboxylate linkage which typically has a structure of R—$CO_2$— (where n is at least 1 and R=alkyl or aryl) and has different chemical and physical properties.

The terms "group" and "moiety" are all used herein interchangeably to refer to a distinct, definable portion or unit of a molecule. Sometimes, the structure of a group or moiety may include another smaller group or moiety. For example, a functional group of —O—$CO_2$—Z includes Z which may be a reactive group or moiety including N-succinimidyl or 1-benzotriazolyl.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

The terms "protected" or "protecting group" or "protective group" refers to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., *PROTECTIVE GROUPS IN ORGANIC SYNTHESIS*, 3rd ed., John Wiley & Sons, Inc., New York, N.Y. (1999).

As used herein, the term "functional group" or any synonym thereof is meant to encompass protected forms thereof.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl, 1-ethylpropyl, 3-methylpentyl, and the like.

"Lower alkyl" refers to an alkyl group containing from 1 to 6 carbon atoms, and may be straight chain or branched, as exemplified by methyl, ethyl, n-butyl, i-butyl, t-butyl.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages that may be employed in a polymer of the invention include but are not limited to carboxylate ester, phosphate ester, anhydrides, acetals, ketals, acyloxyalkyl ether, imines, orthoesters, peptides and oligonucleotides.

The term "biologically active agent" when used herein means any substance that can impact any physical or biochemical properties of a biological organism including, but not limited to, viruses, bacteria, fungi, plants, animals and humans. In particular, as used herein, a biologically active agent can be any substance intended for the diagnosis, cure, mitigation, treatment, or prevention of a disease in humans or other animals, or to otherwise enhance the physical or mental well being of humans or animals. Examples of biologically active agents include, but are not limited to, organic and inorganic compounds, proteins, peptides, lipids, polysaccharides, nucleotides, DNAs, RNAs, other polymers, and derivatives thereof. Examples of biologically active agents include antibiotics, fungicides, anti-viral agents, anti-inflammatory agents, anti-tumor agents, cardiovascular agents, anti-anxiety agents, hormones, growth factors, steroidal agents, and the like. Biologically active agents include microorganisms such as bacteria and yeast cells, viral particles, plant or animal or human cells or tissues, and the like, in their native or modified forms.

II. Polymer of the Invention and Compositions

In general, a polymer of the invention is composed of two or more oligomers covalently linked by a hydrolytically degradable carbonate bond, where each oligomer is a triblock copolymer having a central propylene oxide block or butylene oxide block positioned between two ethylene oxide blocks. Typically, but not necessarily, the oligomeric blocks making up the polymer are the same. The ethylene oxide blocks are poly(ethylene glycol)s with a predetermined molecular weight, typically from about 88 to about 8000, preferably from about 88 to about 2000. Propylene oxide and butylene oxide monomers do not significantly vary the molecular weight of the polymer. Thus, the polymer behaves in a similar manner to polyethylene glycol. However, when delivered in vivo, the polymer will break down into a number of smaller oligomer fragments. If the polymer is conjugated to a biologically active agent, and the linkage between the polymer and the biologically active agent is stable, then, after degradation, one oligomer is linked to the agent.

Pictorially, an oligomer of the invention can be represented as having the following core structure absent specific termini or intervening linkers: -(EO)$_n$-(PO or BO)$_q$-(EO)$_r$-, where EO is ethylene oxide, PO is propylene oxide and BO is butylene oxide. Values for n range from about 2 to about 2000, preferably from about 5 to about 500, and more preferably from about 80 to 120; values for q range from about 2 to about 2000, preferably from about 20 to about 500, more preferably from about 30 to about 250; and values for r range from about 2 to about 2000, preferably from about 5 to about 500, and more preferably from about 80 to 120. More specific exemplary embodiments of an oligomer core of the invention include: -(EO)$_n$-(PO)$_q$-(EO)$_r$, -(EO)$_n$-(BO)$_q$-(EO)$_r$, and -(EO)$_n$-(a combination of PO and BO)$_q$-(EO)$_r$. Preferably, the oligomers are linked by hydrolytically degradable carbonate linkages. However, other suitable linkages include sulfite, thiourea, thiocarbonate, carboxylate ester, phosphate ester, anhydride, acetal, ketal, acyloxyalkyl ether, imine, and orthoester.

The ratios of ethylene oxide and propylene oxide in each of the oligomers of the invention can vary widely, although it is preferable for both the oligomer and the resulting polymer to be water soluble. The ethylene oxide groups generally constitute from about 10% to about 85% by weight of the oligomeric subunits, and thus also of the resulting polymer. Preferred oligomers will possess at least about 40% by weight ethylene oxide subunits, and more preferably at least about 50% by weight ethylene oxide.

The oligomers used in the practice of the invention are selected so that they and the degradation products of the polymer of this invention are water soluble and can easily be excreted from animal bodies under natural physiological conditions. They should be non-toxic, or at least of acceptably low toxicity, and should not cause a substantial adverse effect in human or animal bodies.

Different types of alkylene oxide oligomers are useful in forming the polymer of this invention. Suitable oligomers include alkylene oxide "co-oligomers," which are composed of different alkylene oxide monomers in which R is varied independently along the chain. Oligomers for use in the invention are generally formed from about 2 to about 2000 monomers. In the context of the present invention, a "monomer" typically refers to an ethylene oxide, a propylene oxide or a butylene oxide subunit. Preferred oligomers are composed of from about 5 to 500 monomers, of from about 5 to about 300 monomers, or from about 10 to 50 monomers. An oligomer can be prepared by polymerizing or co-polymerizing monomers, and the size or molecular weight of the oligomer can be controlled by limiting the extent of this polymerization reaction.

A particularly preferred oligomer for use in forming a polymer of the invention

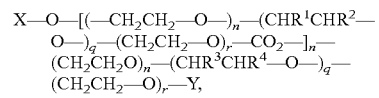

where n, q, r, and m are as described above, and X and Y are each independently selected from the group consisting of H, alkyl, alkenyl, aryl, or a reactive moiety. In the above instance, $R^1$, $R^2$, $R^3$ and $R^4$ are each either alkyl or H, and preferably are either lower alkyl or H. In particular, $R^1$ is H when $R^2$ is alkyl and $R^1$ is alkyl when $R^2$ is H. Further, $R^3$ is H when $R^4$ is alkyl and $R^3$ is alkyl when $R^4$ is H.

Polymer compositions of the invention will generally contain a mixture of polymers having a variety of repeating units, m, where m is generally characterized as an average value. Preferred polymer compositions will have m values ranging from 1 to 20, with a preferred average m value of less than about 15, and even more preferably less than about 10.

In a specific embodiment of the poly (ether carbonate) composed of $(CH_2CH_2-O)_n-(CHRCH_2-O-)_q-(CH_2CH_2-O)$, oligomers, R is methyl. This corresponds to an ethylene oxide-propylene oxide-ethylene oxide (EO-PO-EO) oligomer having interconnecting carbonate linkages.

A polymer of this invention can be prepared to have an inert terminal moiety, typically H, alkyl, and aryl. The alkyl and aryl groups can be substituted or unsubstituted, and normally are methyl, ethyl, phenyl, etc. Most preferred as an end-capping moiety is methyl. The polymer may also be modified, either at one or more termini or by introduction of a pendant group, to possess one or more reactive moieties capable of reacting with a functional moiety in another molecule such as an amino group or a thiol group on a protein. Examples of such reactive moieties include, but are not limited to, acryloyl, alkenyl, tresyl, N-succinimidyloxycarbonyl, 1-benzotriazolyloxycarbonyl, p-nitrophenyloxycarbonyl, N-maleimidyl, aldehydes, acetals, 1-imidazolylcarbonyl, vinylsulfone, iodoacetamide, o-pyridyldithiyl, and the like.

In one embodiment of the invention, the polymer is a poly(ether carbonate) composed of block co-polymer oligomers having an alkylene oxide block positioned between two ethylene oxide blocks, with the formula:

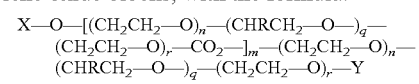

where n, q, and r are independently integers from 2 to about 2000, m is an integer from 1 to about 2000, R can be alkyl, and where X and Y are independently selected from the group consisting of H, alkyl, alkenyl, aryl, or a reactive group and can be the same or different. Reactive groups include but are not limited to acryloyl, tresyl, N-succinimidyloxycarbonyl, 1-benzotriazolyloxycarbonyl, p-nitrophenyloxycarbonyl, N-maleimidyl, aldehydes, acetals, 1-imidazolylcarbonyl, vinylsulfone, iodoacetamide, and o-pyridyldithiyl. The value of n normally is about 80 to about 120, q normally is about 40 to about 70, and m normally is about 1 to about 5.

The poly(ether carbonate) composed of $(CH_2CH_2\text{—}O)_n\text{—}(CHRCH_2\text{—}O\text{—})_q\text{—}(CH_2CH_2\text{—}O)_r$ oligomers can be prepared generally as described herein, or by simply using starting oligomers having $(CH_2CH_2\text{—}O)_n\text{—}(CHRCH_2\text{—}O)_q\text{—}(CH_2CH_2\text{—}O)_r$ groups rather than $(CH_2CH_2\text{—}O)_n$ groups.

The polymer of this invention is typically a linear polymer having two termini. However, branched polymers and star polymers are also contemplated composed of two or more linear polymers, at least one of which corresponds to the linear polymer portions described herein covalently linked to a central branching core.

The invention is meant to include compositions of the above-described polymers. A composition of the invention will generally comprise one or more of the polymers described herein, and may be in the form of a solid, a solution, a suspension, or a gel. Solution compositions of the invention will generally be aqueous, and may contain anywhere from 1 to over 50% by weight polymer. A polymer solution in accordance with the invention may optionally include an active agent. A composition of the invention may also comprise a polymer of the invention in hydrolyzed form. Compositions in accordance with the invention include hydrogels comprising a polymer of the invention, where the hydrogel may additionally include an active agent. The active agent, in either its native or polymer modified form, may simply be associated with the gel, or may be covalently attached thereto. Compositions in accordance with the invention may be provided in combination with a delivery device such as a syringe.

III. Conjugates

An activated polymer of the invention as described above can be reacted with an active group on a biologically active agent, such as a protein or peptide, to form a conjugate. The conjugate comprises the polymer of this invention covalently linked to a biologically active agent. Because the polymer of this invention is hydrolytically degradable in vivo and can be cleaved at the carbonate linkages, thus forming smaller oligomers, the conjugate is especially useful for controlled delivery of the bound agent into animal bodies. Since the polymer in the conjugate is susceptible to breakdown into smaller oligomers, the polymer typically is excreted from animal bodies faster than a polymer of similar size that is not degradable. Thus, potentially adverse effects that may be caused by a large polymer's long period of stay in the body are avoided. Therefore, conjugation of the polymer of this invention to a biologically active agent can provide for a sufficient circulation period for the agent while minimizing any adverse effects of the polymer.

Bioactive agents that may be covalently attached to a polymer of the invention to form a conjugate and/or that may be combined with a polymer or a polymer composition of the invention, in either solution or gel form, include the following. Such agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Specific examples of active agents suitable for use in the invention include but are not limited to calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), bone morphogenic protein-2, acidic fibroblast growth factor, basic fibroblast growth factor, CD-40 ligand, heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, interleukin-17 receptor, luteinizing hormone releasing hormone (LHRH), factor IX insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, transforming growth factor-1, vascular endothelial growth factor, leucaemia inhibiting factor, keratinocyte growth factor (KGF), glial growth factor (GGF), tumor necrosis factor (TNF), endothelial growth factors, parathyroid hormone (PTH), glucagon-like peptide thymosin alpha 1, inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecia, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicllinase-resistant agents like methicillin, oxacillin, cloxacillin, dicloxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

In the conjugates of this invention, the linkage between the biologically active agent and the polymer of this invention can be stable or hydrolytically degradable. When the linkage is degradable, substantially all of the polymer can be cleaved off the biologically active agent under physiological conditions, releasing the agent substantially in its native form inside the body. Methods for forming a hydrolytically degradable linkage between a biologically active agent and a water soluble polymer are well known in the art and should be apparent to a skilled artisan. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include carbonate linkages; imine linkages resulted from reaction of an amine and an aldehyde (see, e.g., Ouchi et al., *Polymer Preprints*, 38(1):582-3 (1997), which is incorporated herein by reference.); phosphate ester linkages formed by reacting an alcohol with a phosphate group; hydrozone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, e.g., at an end of a polymer such as PEG, and a carboxyl group of a peptide; and oligonucleotide linkages formed by a phosphoramidite group, e.g., at the end of a polymer, and a 5' hydroxyl group an oligonucleotide.

Methods for conjugating the polymer of this invention to a biologically active agent should be apparent based on the above discussion. Typically, the polymer of this invention must be activated to form the activated polymer of this invention as described above, having at least one terminal reactive moiety. The terminal reactive moiety may vary depending on the reactivity of a target moiety on the biologically active agent to be conjugated. Examples of reactive groups on proteins are thiols and amines, while on small molecule drugs, amines, alcohols, thiols, and carboxylic acids are common reactive groups. The conjugate is then formed by reacting the terminal reactive moiety of the activated polymer with the target moiety on the biologically active agent. Such methods are well known in the art, and are discussed in the patents and publications referred to above in the context of forming terminal reactive moieties.

For example, N-succinimidyloxy, 1-benzotriazolyloxy, and p-nitrophenyloxy are leaving groups suitable for the formation of a carbamate linkage between the polymer and a biologically active agent having an amino group. Thus proteins, peptides, amino drugs, or amino carbohydrates can be linked to such activated polymers. For example, when X is H, and Y is N-succinimidyloxycarbonyl, a conjugate having the following formula is provided:

HO—[(CH$_2$CH$_2$—O)$_n$—(CHRCH$_2$—O—)$_q$—(CH$_2$CH$_2$—O)$_r$—CO$_2$]$_m$—(CH$_2$CH$_2$—O)$_n$—(CHRCH$_2$—O—)$_q$—(CH$_2$CH$_2$—O)$_r$—CONH-Protein.

When a protein to be conjugated has an accessible thiol group, the polymer of this invention can be activated to contain a terminal reactive moiety that is reactive with thiol, including, for example, iodoacetamide, vinylsulfone, maleimide, or S—S-ortho-pyridyl, which moiety is then reacted with the thiol group to form a thiol site-specific conjugate of the protein.

The specific structure of any conjugate prepared by reaction with a polymer of the invention will depend of course on the reactive coupling sites on the bioactive agent, whether the conjugate is prepared in a random or site specific fashion (and therefore the number of polymers attached to the active agent), and the particular linker or reactive group contained in the polymer.

IV. Hydrogels and Their Thermal Properties

One unique property of the polymers of the invention is their ability to form hydrogels in aqueous solution. A hydrogel is a three dimensional hydrophilic polymeric network capable of imbibing large quantities of water. Such systems typically exhibit excellent biocompatibility. At certain concentrations and temperatures, the polymers of the invention are capable of forming hydrogels. More particularly, the polymers of the invention gel upon an increase in temperature, and do not require the incorporation of additional covalent cross-linking reagents.

The poly(ether carbonate) of the invention, with oligomeric structure of ethylene oxide-alkylene oxide-ethylene oxide, forms a gel composition at certain temperatures. This unique property is due to the ethylene oxide monomers being hydrophilic while other alkylene oxide monomers exhibit hydrophobic properties. The overall hydrophilic or hydrophobic nature of the polymer is determined by temperature, concentration of the polymer in solution, and the type of oligomer used. These polymers exhibit reverse thermal gelation, meaning that the polymers gel upon an increase in temperature.

Those embodiments of the poly(ether carbonate) which exhibit reverse thermal gelation characteristics are thermosensitive polymers. Below certain concentrations of the polymers in solution or below certain temperatures, depending upon the above described composition of the oligomers, the polymers are clear solutions. As the temperature or concentration of the polymers is increased, the polymers absorb water and become viscous gels. If compounds such as drugs are included as solutions or suspensions in aqueous media containing a polymer of this embodiment of the invention, the drug or drugs become entrapped in the polymeric gel when the temperature is raised above the gelation point. The gelation of this embodiment of the invention occurs when the normally heavily hydrated polymer sheds water at elevated temperatures and the more hydrophobic portions of the polymer stick together, and does not require linkage to a backbone molecule such as those typically required for formation of hydrogels.

Aqueous solutions of this thermally reversible gel which contain one or more biologically active agents can be injected as a liquid, for example, subcutaneously or intramuscularly into a mammal, with resultant formation of a gel containing the biologically active agent. The biologically active agent need not be chemically bound to the polymer, as the gelation of the polymer will entrap the biological agent within the polymer matrix when it forms the gel. After a period of time, the carbonate linkages of the gelled polymer degrade by hydration so that the gel slowly degrades and releases the entrapped agents from the gel. During degradation, the therapeutic agents become available for treatment of disease within the body, while the alkyl oxide oligomers are solublized and excreted from the body.

A specific embodiment of the poly(ether carbonate) with thermally reversible gellation characteristics is provided when R is methyl, resulting in a compound of formula:

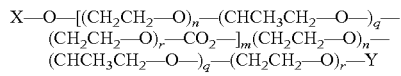

wherein n, q, r, m, X, and Y are as defined above. In general, this embodiment will form a liquid at ambient temperatures and will form a gel at a temperature that is about the body temperature of a mammal. The gelation point, or the temperature at which the polymer begins to gel, depends upon the size of the oligomer and the concentration of the polymer in solution. Both oligomer size and polymer concentration may be varied in order to modify the gelation point.

These forms of poly(ether carbonate) contain repeating alkylene oxide oligomers linked by carbonate linkages that can be hydrolytically cleaved, i.e., the gels are biodegradable. Such hydrolytic cleavage leads to alkylene oxide oligomers and carbon dioxide. Therefore, the poly(ether carbonate) differs substantially from poly(ethylene glycol) or PEG in having multiple degradable backbone carbonate linkages that allow the polymer to be broken down into many smaller oligomers. Since the rate of degradation of the polymer is proportional to the number of degradable carbonate linkages present, and since the size and number of the oligomers can be predetermined, substantial control over both degradation rate and the size of the degradation products is thus possible.

Dissolution characteristics of representative polymers of the invention are described in FIG. 3. As can be seen, the gels of the invention dissolve or degrade slowly over time under physiological conditions. Depending upon the concentration of polymer, a gel of the invention will generally dissolve under physiological conditions in about 10 days to about 150 days, preferably in about 25 days to about 100 days. The dissolution rates can be customized by the number of carbonate linkages in the polymer, the particular composition of the oligomeric components and the like.

The reverse thermal properties of an exemplary polymer of the invention in aqueous solution are plotted graphically in FIG. 1. The polymers of the invention are typified by a low viscosity at temperatures ranging from about 4° C. to about 80° C. depending upon concentration. More importantly, the polymers of the invention are solutions at temperatures less than about 25° C. at concentrations ranging from over 20% by weight to less than 5% by weight, while they form gels at temperatures ranging from about 25° C. to over 70° C. In looking at the behavior of aqueous compositions of the polymers at body temperature (37° C.), it can be seen that the polymers form gels at concentrations as low as 5% by weight. This is a marked improvement over the gelation properties of materials such as monomeric poloxamer 407, which forms a gel at high temperatures only at concentrations exceeding 16 weight percent. Thus, one can employ formulations of the present polymers at concentrations that are less than half those of the commercially available poloxamer 407.

Moreover, the polymers of the invention can be injected as solutions that form hydrogels in vivo upon administration. Such reverse thermal gelation characteristics are useful for administering biologically active agents to mammals. The polymer and a suitable drug, protein, or enzyme, can be injected into the general circulation of a mammal. Upon administration, the polymer forms a gel due to the increase in temperature in the body, to thereby provide an in-vivo generated hydrogel that can be used as a drug carrier, e.g., having a biologically active agent entrapped therein. This leads to a much greater ease of delivery when compared to gels that must be surgically implanted.

The gels of the invention may additionally contain drugs in their native form or that are polymer-modified. As can be seen in the Examples, the polymers of the invention, when in hydrogel formulations, were particularly effective in providing sustained release of bioactive agents that had been modified by polymer attachment. The hydrogels of the invention provided prolonged release of pegylated drugs over periods ranging from one to over 160 hours, thus demonstrating the potential of these hydrogels as depot drug carriers.

When the polymer of this invention is activated at two termini, it can be used as a crosslinking agent to crosslink a multifunctional molecule to form a crosslinked hydrolytically degradable hydrogel, distinct from the thermally reversible gel, which is not covalently crosslinked. A crosslinked hydrogel typically is a polymeric network formed by crosslinking one or more multifunctional backbone molecules or polymers. The resulting polymeric network is hydrophilic and swells in an aqueous environment thus forming a gel-like material, i.e., hydrogel. Hydrogels of this type are also useful for drug delivery as they can be implanted or injected into animal bodies. Typically a hydrogel comprises a backbone bonded to a crosslinking agent.

Examples of multifunctional molecules suitable as "backbones" in formation of hydrogels include proteins such as collagen, aminocarbohydrates such as chitosan, polyamines such as polylysine and poly(vinylamine), and multi-armed or branched poly(ethylene glycol) amines. A polymer of this invention can be activated by attachment of, for example, terminal vinyl groups. This activated polymer can be self-polymerized in the presence of a conventional vinyl polymerization catalyst to form a crosslinked hydrolytically degradable hydrogel different from those gels described above.

As stated above, the polymer of this invention can be used as the crosslinking agent in a chemically cross-linked hydrogel. The polymer must be activated so that it has at least two terminal reactive moieties that are capable of reacting with multiple moieties on the backbone to form covalent linkages.

Alternatively, two or more types of activated polymer may be used as crosslinking agents. Each activated polymer has one terminal reactive moiety capable of reacting with a moiety on the backbone, and another terminal reactive moiety capable of reacting with the corresponding terminal reactive moiety on the other type of activated polymer. An example of this other moiety is, for example, a vinyl-containing group such as an acrylate group that can participate in chain polymerization among the different types of activated polymers. When the polymer of this invention is activated so that it has two terminal vinyl groups, the polymer itself may act as both crosslinking agent and backbone, and self-polymerize into a hydrolytically degradable hydrogel through a chain polymerization reaction.

The backbone of a crosslinked hydrogel is generally a nontoxic biocompatible macromolecule or small molecule, having at least two or preferably more active groups available to react with the terminal reactive moieties of the crosslinking agent to form covalent linkages. By "biocompatible" it is intended that the molecule used as backbone would not substantially adversely affect the body and tissue of the living subject into which the hydrogel is to be implanted or injected.

More particularly, the material does not substantially adversely affect the growth and any other desired characteristics of the tissue cells surrounding the implanted hydrogel. It is also intended that the material used does not cause any substantially medically undesirable effect in any other parts of the living subject. In addition, if the molecule is degradable inside the body, the degradation products should also be substantially biocompatible as defined above. Generally, the methods for testing the biocompatibility of a material are well known in the art.

Examples of suitable backbones include, but are not limited to, proteins, modified proteins such as glycoproteins, phosphorylated proteins, acylated proteins, and chemically modified proteins, peptides, aminocarbohydrates, glycosaminoglycans, aminolipids, polyols, polythiols, polycarboxylic acids, polyamines such as dilysine, poly(vinylamine) and polylysine, poly(ethylene glycol) amines, pharmaceutical agents having at least two active groups, etc. Specific examples of the backbone include, but are not limited to, branched PEG amines, fibrin, fibrinogen, thrombin, albumins, globulins, collagens, fibronectin, chitosan, and the like. In addition, the backbone may also be microorganisms such as viral particles, bacterial or yeast cells, animal or human cells or tissues.

The activated polymer of this invention used as a crosslinking agent can be in a linear, branched or star form. In branched or star forms, three or more linear polymers are covalently linked, at one terminus, to a central, branched core moiety. The central branch core moiety can be derived from the amino acid lysine, or polyols such as glycerol, pentaerythritol and sorbitol. Branched PEGs are known in the art. These branched PEGs can be incorporated as components of the poly(ether carbonate)s of this invention.

As will be apparent, because of the carbonate linkages incorporated in the crosslinking agent, the hydrogel of this invention is hydrolytically degradable. In addition, the linkages between the backbones and the crosslinking agents formed from the crosslinking reactions can also be made hydrolyzable, by methods described in the context of the conjugate of this invention. Thus, the hydrogel of this invention can gradually break down or degrade in the body as a result of the hydrolysis of the hydrolytically degradable linkages.

V. Methods of Making the Polymers

To prepare polymers of the invention, in one example, one or more oligomers as described above are provided each having a hydroxyl group at one terminus and a functional group of —O—$CO_2$—Z at another terminus. The oligomers are then polymerized or co-polymerized in a condensation polymerization reaction under conditions sufficient to form a hydrolytically degradable polymer.

The functional group —O—$CO_2$—Z is capable of reacting with a hydroxyl group to form a carbonate linkage. Typically, Z can be any reactive leaving groups so long as the functional group can react with a hydroxyl group to form a carbonate linkage. Examples of suitable leaving groups include N-succinimidyl, 1-benzotriazolyl, and p-nitrophenyl. Methods for preparing an oligomer having a functional group —O—$CO_2$—Z as described above are well known in the art, and are disclosed in U.S. Pat. Nos. 5,650,234, 5,281,698 and 5,468,478; Veronese, et al., *Appl. Biochem. Biotech.*, 11:141 (1985); and Sartore et al., *Appl. Biochem. Biotech.*, 27:45 (1991), all of which are incorporated herein by reference.

More particularly, a polymer of the invention may be prepared as follows. A first oligomer is provided, which is a bifunctional oligomer having a first functional group of —O—$CO_2$—W at one terminus and, at another terminus, a second functional group of —O—$CO_2$—Z. Both functional groups are capable of reacting with a hydroxyl group to form a carbonate linkage. Z and W are reactive leaving groups, and can be any leaving groups known in the art so long as the functional groups containing them, as stated above, are capable of reacting with a hydroxyl group to form a carbonate linkage. Z and W can be same or different. The preferred Z and W are N-succinimidyl, 1-benzotriazolyl, and p-nitrophenyl. Two or more different bifunctional oligomers can also be used in the same polymerization reaction.

Methods for preparing such bifunctional oligomers are similar to those for making the monofunctional oligomers described above. Preferably, Z and W are the same, and the bifunctional molecule Z-oligomer-Z can be provided by activating an oligomer having two hydroxyl terminal groups, with an activating molecule having the formula of Z—O—$CO_2$—Z. Suitable examples of the activating molecule include, disuccinimidylcarbonate, bis(1-benzotriazolyl) carbonate and bis(p-nitrophenyl) carbonate. See, e.g., U.S. Pat. No. 5,281,698; U.S. Pat. No. 5,650,234; Veronese, et al., *Appl. Biochem. Biotech.*, 11:141 (1985); and Sartore et al., *Appl. Biochem. Biotech.*, 27:45 (1991), all of which are incorporated herein by reference.

In addition to the first oligomer that is bifunctional, a second oligomer is also provided having two terminal hydroxyl groups. This second oligomer is then polymerized with the first oligomer to form the polymer of this invention.

Two or more types of bifunctional oligomers can be used in the same polymerization reaction. In addition, two or more types of oligomers having two terminal hydroxyl groups can also be used in a polymerization reaction. As will be apparent to a skilled artisan, when only one type of bifunctional oligomer and one type of dihydroxyl oligomer are used, and when the two oligomers are the same except for the terminal groups, the polymer formed therefrom will be a homopolymer having a single type of repeating unit or oligomer linked with hydrolytically degradable linkages. Otherwise, a heteropolymer or block polymer or terpolymer will be made containing different types of oligomers in the polymer backbone.

In yet another method, one or more oligomers having two hydroxyl terminal groups are polymerized directly with an activating molecule having the formula of Z—O—$CO_2$—Z to form the hydrolytically degradable polymer. In this method, either one oligomer is used to generate a homopolymer, or two or more different oligomers can be used in the same polymerization reaction to produce a heteropolymer, or block polymer or terpolymer.

The polymerization reactions are conducted under conditions sufficient to form the hydrolytically degradable polymer of this invention. The polymerization reaction in each of the above-described methods is a condensation reaction. Many different known reaction conditions can be used. Typically, a catalyst is included in the polymerization reaction mixture. Examples of suitable catalysts are organic bases, including triethylamine, pyridine, quinoline, and 4,4-dimethylaminopyridine. Amine bases such as 4,4-dimethylaminopyridine and triethylamine are preferred.

The polymerization can be conducted in either melt or solvent. Suitable solvents include, but are not limited to, acetonitrile, THF, dimethylformamide, dimethylsulfoxide, benzene, toluene, xylenes, chloroform, and methylene chloride. The polymerization reaction rate and the extent of polymerization, which determines the average molecule weight of the final hydrolytically degradable polymer product can be partly controlled by the reaction temperature and the reaction time. Suitable reaction temperature can vary from about 0° C. to 100° C. Higher reaction temperatures lead to greater reaction speed. Preferably, the polymerization reaction is conducted at a temperature of from about 37° C. to 100° C., typically from about 45° C. to 100° C. and advantageously from about 70° C. to 90° C. When the reaction is conducted in a melt, the temperature needs be maintained at a certain minimum temperature in order to keep the reaction mixture at a melt state.

In the above described three embodiments of the method of this invention, the polymerization reactions would be predicted to lead to polymers with an activated carbonate terminal group. In practice, however, NMR analysis of the polymer products indicates that the terminal groups of the hydrolytically degradable polymer prepared therefrom often are hydroxyl groups. While not wishing to be bound by any theory, it is believed that this is caused by reaction with a small amount of water present as an impurity in the reaction. Any small amount of remaining terminally activated carbonate may be removed by hydrolysis in water for a short period or near a neutral pH. The terminal activating groups are much more sensitive to water than are the degradable carbonate linkages.

The polymer of this invention can optionally be activated at one or all termini, thus providing an activated polymer capable of being covalently linked to another molecule, including, for example, a protein, to form a conjugate. The polymer can also be capped at one terminus by an inert group and at another terminus by a reactive moiety.

The polymer of this invention can be activated at its terminus to form a terminal reactive moiety by methods well known to those familiar with the art of organic or polymer chemistry. The well established methods in the broad field of poly(ethylene glycol) chemistry are generally useful, and such methods should be apparent to a skilled artisan. The polymer can be activated at one terminus, or all termini, in which case, the reactive moieties at different termini can be same or different.

For example, the polymer may be activated to form a terminal moiety of N-succinimidyl carbonate (see e.g., U.S. Pat. Nos. 5,281,698, 5,468,478), amine (see, e.g., Buckmann et al. *Makromol. Chem.* 182:1379 (1981), Zaplipsky et al. *Eur. Polym. J.* 19:1177 (1983)), hydrazide (See, e.g., Andresz et al. *Makromol. Chem.* 179:301 (1978)), succinimidyl propionate and succinimidyl butanoate (see, e.g., Olson et al. in *Poly(ethylene glycol) Chemistry & Biological Applications*, pp 170-181, Harris & Zaplipsky Eds., ACS, Washington, D.C., 1997; see also U.S. Pat. No. 5,672,662), succinimidyl succinate (See, e.g., Abuchowski et al. *Cancer Biochem. Biophys.* 7:175 (1984) and Joppich et al. *Macrolol. Chem.* 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. *Eur. J. Biochem.* 94:11 (1979), Elling et al., *Biotech. Appl. Biochem.* 13:354 (1991), oxycarbonylimidazole (see, e.g., Beauchamp, et al., *Anal. Biochem.* 131:25 (1983), Tondelli et al. *J. Controlled Release* 1:251 (1985)), p-nitrophenyl carbonate (see, e.g., Veronese, et al., *Appl. Biochem. Biotech.*, 11:141 (1985); and Sartore et al., *Appl. Biochem. Biotech.*, 27:45 (1991)), aldehyde (see, e.g., Harris et al. *J. Polym. Sci. Chem. Ed.* 22:341 (1984), U.S. Pat. No. 5,824,784, U.S. Pat. No. 5,252,714), maleimide (see, e.g., Goodson et al. *Bio/Technology* 8:343 (1990), Romani et al. in *Chemistry of Peptides and Proteins* 2:29 (1984)), and Kogan, *Synthetic Comm.* 22:2417 (1992)), orthopyridyl-disulfide (see, e.g., Woghiren, et al. *Bioconj. Chem.* 4:314 (1993)), acrylol (see, e.g., Sawhney et al., *Macromolecules*, 26:581 (1993)), vinylsulfone (see, e.g., U.S. Pat. No. 5,900,461). In addition, two molecules of the polymer of this invention can also be linked to the amino acid lysine to form a di-substituted lysine, which can then be further activated with N-hydroxysuccinimide to form an active of N-succinimidyl moiety (see, e.g., U.S. Pat. No. 5,932,462). All of the above references are incorporated herein by reference.

To give an example, the polymer of this invention may be activated to form a terminal reactive moiety of N-succinimidyl carbonate or 1-benzotriazolyl carbonate by reacting the polymer with di-N-succinimidyl carbonate or di-1-benzotriazolyl carbonate respectively. To give another example, terminal reactive moieties such as N-maleimidyl and o-pyridyldithiyl may be prepared by reacting the polymer with activated carbonates connected to N-maleimidyl or o-pyridyldithiyl by linker groups. Terminal aldehyde and acetal moieties can be attached by linking groups. Terminal acid groups can be attached by reaction of the above active carbonates with amino acids or other acid linkers. These acids can then be activated by formation of active esters such as succinimidyl active esters.

The polymer of this invention, activated or not, as prepared by the above methods, can be purified from the reaction mixture. Many methods known in the art can be used. A preferred method for purifying the polymer and its derivatives is by precipitation from a solvent in which they are essentially insoluble while the reactants are soluble. Suitable solvents include ethyl ether or isopropanol. As is apparent to a skilled artisan, other methods such as ion exchange, size exclusion, silica gel, and reverse phase chromatography can also be useful.

VI. Utility

The hydrogels of this invention are useful in many biomedical applications such as drug delivery, surgical adhesion prevention, wound and scar healing, bioadhesives and surgical implants.

Specifically, the hydrogel of this invention is suitable as a biomedical material and a carrier for the delivery of biologically active agents. For example, the hydrogel can carry therapeutic drugs and can be implanted or injected in a target area of the body. The hydrogel may also carry other agents such as nutrients or labeling agents for imaging analysis. A hydrogel containing a biologically active agent is termed herein as "a delivery system".

In the various applications of the hydrogel of this invention, the biologically active agents to be delivered can be used as the backbone, or part of the backbone of the hydrogel. Alternatively, biologically active agents can be "hinged" to the hydrogel through a polymer of this invention or a linker molecule with one terminus of the polymer or the linker linked to the biologically active agent, and the other being connected through a covalent linkage to the hydrogel. In addition, biologically active agents or other substances to be delivered can also be loaded into the hydrogel during the formation of the hydrogel, or afterwards by, for example, diffusion into the matrix of the hydrogel without being covalently bonded to the hydrogel structure.

Because the polymers of this invention in the hydrogel are water soluble, the hydrogel can be substantially water swellable. The degradation or breakdown of the hydrogel in the body is gradual in nature and subject to control because of the hydrolytically degradable carbonate linkages in the polymer. Thus, the hydrogels of the invention, whether formed by crosslinking or reverse thermal gelation, are particularly useful for sustained release of a biologically active agent or other substance in the body.

The present invention is further illustrated in the following examples which are given to illustrate the invention, but should not be considered in limitation of the invention.

EXAMPLES

Materials and Methods $^1$H NMR data was obtained using a 300 MHz spectrometer manufactured by Bruker.

PEG reagents referred to in the appended examples are available from Shearwater Corporation, Huntsville, Ala.

Pluronic™ F127-NF (also referred to herein as Poloxamer 407) was obtained from BASF Corporation, Mt. Olive, N.J. Pluronic™ F127-NF is a triblock copolymer of ethylene oxide and propylene oxide having the formula HO—$(CH_2CH_2O)_x$—$(CH_2CHCH_3O)_y$—$(CH_2CH_2O)_x$—H, where x on average equals 98 and y on average equals 67.

The oligomeric product (I) was further characterized by gel permeation chromatography as having the following structure HO—[$(CH_2CH_2O)_{98}$—$(CH_2CHCH_3O)_{67}$—$(CH_2CH_2O)_{98}$—CO2]$_m$—[$(CH_2CH_2O)_{98}$—$(CH_2CHCH_3O)_{67}$—$(CH_2CH_2O)_{98}$—H, where m ranged from about 1 to about 5 with an average value of about 2.

Thus, on average, the polymer product was composed of three "P407" subunits connected by two carbonate linkages as described structurally above. (In an abbreviated format, the product is represented as HO[P407-CO2]$_m$P407-H, where the P407 portion is represented as [—$(CH_2CH_2O)_{98}$—$(CH_2CHCH_3O)_{67}$—$(CH_2CH_2O)_{98}$-], and m is as described above.

The overall synthetic approach employed is provided below as Scheme I.

Scheme I. Preparation of an Exemplary Polymer of the Invention

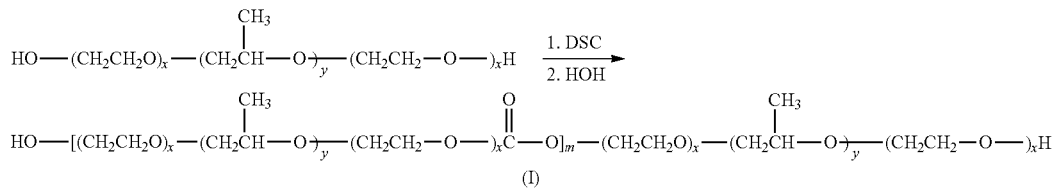

Example 1

Synthesis of a Hydrolytically Degradable Oligomer Composed of Copolymer Subunits of Ethylene Oxide-Propylene Oxide-Ethylene Oxide Covalently Linked by Carbonate Bonds, (I)

An illustrative polymer of the invention was synthesized as follows by coupling to one another block copolymers each composed of a propylene oxide block (i.e., a series of propylene oxide monomers) sandwiched between two ethylene oxide blocks, where the block copolymers are covalently attached to one another by intervening carbonate bonds to form the resulting oligomer.

Poloxamer 407 (10.0 g, 0.78 mmole) was dissolved in 30 ml of $CH_3CN$ in a 50 ml round-bottom flask fitted with a Dean-Stark trap and a reflux condenser. The solution was heated to reflux and 20 ml of solvent was collected. After the Dean-Stark trap was removed, di-(N-succinimidyl) carbonate, DSC (1.1 equivalents, 0.22 g, 0.86 mmole), available from Fluka, and 4-dimethylaminopyridine, DMAP (2 equivalents, 0.19 g, 1.56 mmole) available from Acros, were added and the mixture refluxed for 48 hours. The solvent was then removed from the resulting solution by rotary evaporation and the remaining crude residue was dissolved in 50 ml of sodium phosphate buffer solution (0.1 M, pH=7.0). The aqueous layer was extracted with methylene chloride (3×25 ml). The combined organic layers were dried with sodium sulfate and concentrated to 20 ml. Isopropanol (75 ml) was added to precipitate the product, which was then collected by filtration. The precipitate was washed with 25 ml of ethyl ether and dried under vacuum to yield 5 g of product.

The product (I) was characterized by $^1$H NMR spectroscopy. $^1$H NMR (DMSO-$d_6$)(300 MHz) δ: 4.58 (t, O$\underline{H}$, δ4.18 (t, C$\underline{H}_2$), δ4.11 (t, C$\underline{H}_2$), δ3.5 (bs, —C$\underline{H}_2$C$\underline{H}_2$—), δ1.04 (d, —C$\underline{H}_3$). The peak at 4.18 ppm demonstrated formation of the carbonate bond, while the reduction in area of the peak at 4.58 ppm indicated positionally where the reaction occurred—i.e., at the polymer terminus.

A similar synthesis was carried out using the diamino-form of Poloxomer 407 as the starting material rather than the hydroxy form as shown above. The resulting product, (II), was a polymer characterized as having the same average number of x, y, and m subunits as (I) above, with the exception that the oligomeric subunits were connected by urea linkages (—NH—C(O)—NH—) rather than carbonate linkages.

Example 2

Sol-Gel Characteristics of a Hydrolytically Degradable Oligomer Composed of Triblock Copolymer Subunits of Ethylene Oxide-Propylene Oxide-Ethylene Oxide Covalently Linked by Carbonate Bonds, (I)

The oligomeric product, (I), from Example 1 above was dissolved in phosphate buffer (0.1 M, pH 7.0) at 4° C. at a number of different concentrations. The aqueous polymer-containing solutions were placed in a temperature-controlled water-bath. The temperature of the water bath was slowly increased, and the temperature at which each of the solutions became a solid gel (based upon visual inspection) was recorded.

The sol-gel phase transition was then further refined by monitoring gel formation within two minutes after solutions of (I) at 4° C. were placed in a water bath at preset temperatures. The data was then used to generate a phase diagram demonstrating the sol-gel behavior of (I) at different concentrations and temperatures and is shown as FIG. 1.

In looking at FIG. 1, it can be seen that at temperatures below about 25° C., aqueous solutions of the illustrative polymer (I) remained in solution phase, regardless of the concentration of polymer. However, at temperatures ranging from about 25° C. to about 70° C., a sol-gel phase transition was observed. At temperatures ranging from about 25° C. to 30° C., aqueous solutions of polymer (I) formed gels at concentrations ranging from about 8 to about 20 weight percent, but were solutions at concentrations below about 8% by weight.

At 37° C., aqueous solutions of polymer (I) remained solutions at concentrations below about 5 weight percent, while at concentrations greater than about 5% by weight (i.e., from about 5% by weight to about 20% by weight or more) at this temperature, aqueous solutions of polymer (I) formed gels. Additional temperatures and corresponding weight percentages at which this exemplary oligomer of the invention exists as a hydrogel can be readily determined from FIG. 1.

The sol-gel transition was observed to be reversible. For example, the gel formed at 37° C. became a free-flowing liquid at 4° C. in about two minutes. Thus, in general, the polymers of the invention, when in aqueous solution, can be characterized as forming thermally-reversible or thermal sensitive gels. That is to say, they are polymers whose phase can be reversibly changed from a solution to a gel upon a change in temperature.

The polymers of the invention, when in aqueous solution, form gels at concentrations as low as about 5% by weight, making these polymers particularly attractive for biological applications where low concentrations of administered polymer are desirable. Moreover, the polymers of the invention are a marked improvement over commercially available triblock copolymers such as Poloxomer 407, since they form gels at much lower concentrations than their commercially available counterparts. For example, Poloxomer 407, when in aqueous solution at a temperature near 37° C., forms a gel only at concentrations greater than about 16 weight percent, while an illustrative polymer of the invention, (I), forms a hydrogel at much lower concentrations, i.e., from about 5 to 8% by weight, at the same temperature.

Example 3

Gel Formation and Degradation of (I)

The following illustrates another advantage of the polymers of the invention, i.e., their biodegradability.

Polymer (I) was dissolved in phosphate buffer (0.1 M, pH 7.0) at 4° C. to final concentrations of 5%, 8%, 10%, 12% 15% and 18 wt %, respectively. The aqueous solutions (1 ml) were then each placed in an incubator at a temperature of 37° C. to form a gel. To the gel, 2 ml of phosphate buffer was added and the mixtures were then held at 37° C. until a solution formed. The dissolution of each of the gels at 37° C. was mainly due, not to a physical phase change, but due to their hydrolytic degradation over time (i.e., hydrolysis of the carbonate bonds). The dissolution of these representative gels over time is shown graphically as FIG. 2.

As can be seen from the dissolution data, dissolution times for each of the gel compositions increased with increasing polymer concentration of the gel. For example, the 5 wt % gel dissolved in about 25 days, the 10 wt % gel dissolved in about 40 days, and the 18 wt % gel dissolved in about twice that time or 80 days. Thus, desired dissolution rates can be tailored by adjusting the polymer concentration of the gel to achieve a desired degradation or dissolution rate.

Example 4

Release of Model Drugs from Hydrogels of (I)

Three fluorescein isothiocyanate (FITC)-dextran samples, having molecular weights of 4.4 kDa, 19.5 kDa, and 77 kDa, respectively, were used as model compounds to demonstrate the versatility of the polymers of the invention, e.g., as potential drug carriers capable of providing sustained release of a therapeutic agent over time.

A 10 weight percent solution (1 ml) of (I) was mixed with 30 mg of each of the FITC dextran samples. The resulting solutions were then each injected into a dialysis tube (MWCO 100 kDa), and twenty five ml of preheated phosphate buffer (0.1 M, pH 7.0, 37° C.) was added to an outer test tube. Upon addition of preheated buffer, the solutions each formed gels. The entire system was then placed in an incubator at 37° C. 0.5 ml samples were taken from the outer (dialyzed) solutions every 2 hours and UV absorbance at 490 nm was recorded. This absorbance values were then compared to the dextran calibration curves, and the dextran concentration determined at each time point. The release profiles are shown in FIG. 3.

The profiles reveal that about 40% of the 19.5 dextran kDa sample was released during the first several hours, with an additional 30% of the dextran released steadily over a 50 hour time period. The 77 kDa dextran sample showed a steady release rate over time to a total release of about 30% at 120 hours.

In looking at this data, it can be seen that the polymers of the invention can be used as drug carriers to provide sustained release of therapeutic agents. Moreover, these polymers possess the additional advantage of injectability, that is to say, when co-formulated with drugs at low temperatures, these polymers are free-flowing solutions that can be administered, for example, by subcutaneous injection, to then form gels in-situ. These in-situ generated gels can then provide sustained release of any active agent contained therein. Moreover, the polymers of the invention, by virtue of their in-situ gel forming capabilities, do not have to be implanted, as is the case with most conventional gel-based depot systems.

Example 5

Release Profile of PEG-Biphalin and Biphalin from a Hydrogel of (I)

The following study was undertaken to further examine the release characteristics of a hydrogel of (I) using as a model compound the drug, biphalin, a water-soluble, small peptide analgesic, in both is pegylated and non-pegylated forms.

A. Preparation of $(mPEG_{2K})_2$-Biphalin:

Biphalin (21.1 mg, 0.046 mmol) was dissolved into 15 ml of anhydrous acetonitrile and treated with 16 µl of triethylamine (0.115 mmol, 2.5 fold molar excess). At the same time, $mPEG_{2K}$-succinimidyl propionate (Shearwater Corporation, 110 mg, 0.055 mmol, 1.2 fold molar excess) was dissolved into 5 ml of acetonitrile. The dissolved $mPEG_{2K}$-SPA was slowly added into the above biphalin solution and the reaction mixture was stirred 66 hours at room temperature under nitrogen atmosphere.

Di-pegylated [$(mPEG_{2K})$-2-biphalin] and monopegylated biphalin [$mPEG_{2K}$-biphalin] were separated from unreacted PEG and free biphalin on a Vydac C18 reverse-phase column at 1 ml/min and 215 nm UV detector using a gradient elution of 30% to 60% solvent B. Solvent A is 0.1% TFA in water and solvent B is 0.1% TFA in acetonitrile.

B. Gel Compositions with Biphalin and PEG-Biphalin 60 mg of (I) and 5 mg of $(mPEG_{2K})$-2-biphalin (MW 4900 daltons) or native biphalin (MW 909 daltons) were dissolved in 0.5 ml of phosphate buffer (0.1 M, pH 7.0) at 4° C. 0.3 ml of each of these solutions was injected into a dialysis tube (0.5 ml, MWCO 100 kDa). The dialysis tubes containing solutions of (I) and either biphalin or pegylated biphalin were each placed in a screw-cap test tube at 37° C., and rapid gelation of the solutions was observed. After 5 minutes, 5.7 ml of phosphate buffer was added to each test tube. At 30 minute and one hour intervals, the solution in each test tube (containing drug released from the gel) was analyzed by reverse phase-HPLC for PEG-biphalin or biphalin, and the concentration of each was determined.

The results are presented in FIG. 4. This figure is a plot of the release (in terms of percentage by weight) of both biphalin and pegylated biphalin from a hydrogel of (I) over time. While the unmodified drug, biphalin, was released fairly rapidly from the gel (approximately 80% by weight of the drug was released from the gel in less than about two hours), a representative pegylated form of biphalin was released slowly from the gel over an extended period of time. The difference in the overall release profiles can be seen in FIG. 4. In the first 25 hours, pegylated biphalin was released steadily from the gel. In the first approximately 6 hours, about twenty percent by weight of the drug had been released from the gel. By about twenty five hours, approximately 85% by weight of pegylated biphalin had been released, with release of drug continuing in a steady fashion up to and exceeding the seventy five hour time point. This data, and in particular, data for pegylated biphalin, demonstrate the utility of compositions of the polymers of the invention as depot drug carriers for providing sustained release of therapeutic agents, particularly pegylated therapeutic agents.

Example 6

Release Profiles of a PEG-Fab Fragment and a Fab Fragment from a Hydrogel of (I)

Additional release profile data was generated to further explore the release characteristics of an illustrative gel of the invention when combined with a model therapeutic agent, an illustrative Fab fragment, having a high molecular weight. Antibodies such as the Fab employed can be obtained from commercial sources such as Acris or Protos ImmunoResearch.

180 mg of oligomer (I) was dissolved in 2 ml of buffer (0.1M pH 7.0) which contained either an illustrative Fab fragment (Mw 48.5 kDa) or its PEGylated form prepared by covalently attaching a 30 KDa PEG (MW 78.5 kDa) at 4° C. overnight. Two milliliters of each solution were transferred to vials held at 37° C. for 8 minutes; each solution rapidly gelled upon transfer to the higher temperature environment. Twenty milliliters of sodium phosphate buffer (0.1M, pH 7.0) were added to each vial at 37° C. for the release study. At timed intervals, 0.2 ml aliquots of the solution above each gel were withdrawn and stored at 4° C. for protein concentration analysis by the bicinchoninic acid (BCA) assay method (Pierce). The results were plotted and are presented below as FIG. 5.

As can be seen from FIG. 5, both the Fab fragment and the pegylated Fab fragment were released slowly from the gel, although release of the PEG Fab fragment from the gel occurred over an extended period compared to the parent Fab fragment. While controlled release was observed for both forms of model drug, delivery of the pegylated form appeared particularly advantageous since essentially all of the drug was released from the gel over the time period monitored, and in a steady and sustained fashion. However, use of the gels of the invention can also be advantageous for delivery of non-pegylated drugs, particularly when release of drug is governed not only by diffusion from drug from the intact gel, but rather by degradation of the gel by hydrolysis of its degradable linkages.

Example 7

Synthesis of an Oligomer Composed of Copolymer Subunits of Ethylene Oxide-Propylene Oxide-Ethylene Oxide Covalently Linked by Urea Bonds, (IV)

Another illustrative polymer of the invention, having stable urea rather than degradable carbonate linkages, was prepared as follows. The polymer was prepared from an illustrative amino-terminal triblock copolymer having a polypropylene block sandwiched between two ethylene oxide blocks. The resulting polymer has features similar to (I), with the exception of having stable rather than degradable linkages. The invention is generally meant to encompass such polymers, that is, polymers having stable linkages connecting the oligomeric portions.

A. Poloxamer 407 Mesylate (II):

Poloxamer 407 (50.9 g, 7.83 mmol[OH]) was dissolved in 250 ml toluene and stirred under nitrogen in a 500 mL two-necked round-bottom flask fitted with a Dean-Stark trap and reflux condensor. Poloxamer 407 was azeotropically distilled, then the reaction was cooled to room temperature. Anhydrous di-chloromethane (100 ml) was added via cannula. Distilled triethylamine (6.5 ml, 6 eq) was added via syringe with constant stirring. Methanesulfonylchloride (4 ml, 5 eq) was added via syringe and the reaction was stirred overnight at room temperature under nitrogen. To destroy any unreacted methanesulfonylchloride, ethanol (100 ml) was added and the mixture stirred for 30 minutes. Sodium carbonate (30 g) was added and the mixture was stirred for one hour. The mixture was filtered and concentrated by rotary evaporation followed by high vacuum. The crude material was redissolved in 200 ml solvent. Diethyl ether (800 ml) was added to precipitate the product, which was collected by filtration and dried under high vacuum to provide 50 grams of material. $^1$H NMR (dmso-$d_6$): δ 1.05 (d, C$\underline{H}_3$), 3.18 (s, 6H), 3.54 (m, 109H), 4.38 (m, 4H)

B. Poloxamer 407 Amine (III):

Ammonium chloride (70 g) was dissolved in concentrated ammonium hydroxide solution (700 ml). Poloxamer 407 mesylate (50 g) was added with constant stirring at room temperature. The reaction was heated to 40° C. and stirred for 48 hours with adequate venting to prevent pressure buildup. The reaction was then cooled to room temperature and transferred to a separatory funnel. The solution was extracted with dichloromethane (4×200 ml). The combined organic layers were dried with sodium sulfate (50 g) then filtered and concentrated by rotary evaporation. 2-propanol (500 ml) was added to precipitate the product which was collected by filtration and dried under high vacuum to yield 31.6 grams of material. $^1$H NMR (dmso-$d_6$): δ 1.05 (d, C$\underline{H}_3$), 2.98 (t, 3.8H), 3.54 (m, protons in backbone). $H_2N-[(CH_2CH_2O)_{98}-(CH_2CHCH_3O)_{67}-(CH_2CH_2O)_{97}-CH_2CH_2NH_2$.

C. Oligomer with Urea Linkages (IV):

Oligomer (IV) was prepared using triphosgene as the coupling reagent rather than DSC, although either approach works. The synthesis of a polymer of the invention using triphosgene was found to be particularly beneficial, since excess triphosgene contaminants readily removed by washing, making the work-up of the reaction much simpler and also provides higher purity polymer.

Poloxamer 407-amine (13 g, 1 mmol) was dissolved in acetonitrile (50 ml) and azeotropically distilled using a Dean-Stark trap; removing 35 ml of solvent in the process. The solution was then cooled down to ~30-40° C. and the Dean-Stark trap removed. DMAP (0.37 g, 3 eq) was added. Triphosgene (90 mg, 0.3 eq) was quickly added under nitrogen and with vigorous stirring. The reaction mixture was refluxed overnight. The reaction was cooled to room temperature. Isopropanol (50 ml) and diethyl ether (50 ml) were added to precipitate the product, which was collected by filtration and dried under high vacuum. (12.3 grams) $^1$H NMR (dmso-$d_6$): δ1.05 (d), 3.54 (m), 5.96 (t).

The oligomeric product (IV) possesses the following generalized structure: $H_2N$—[$(CH_2CH_2O)_{98}$—$(CH_2CHCH_3O)_{67}$—$(CH_2CH_2O)_{97}$—$(CH_2CH_2NHC(O)NH]_m$—[$(CH_2CH_2O)_{98}$—$(CH_2CHCH_3O)_{67}$—$(CH_2CH_2O)_{97}$—$CH_2CH_2NH_2$, where the average value of the repeat unit was three, as characterized by gel permeation chromatography.

The foregoing description is to be considered illustrative rather than descriptive of the invention. Therefore, it should be understood that the specific embodiments described herein are illustrative of how the invention may be practiced and that modifications and other embodiments are intended to be included within the scope of the appended claims.

It is claimed:

1. An in-vivo gel-forming composition comprising:
   (i) a polymer having the formula:

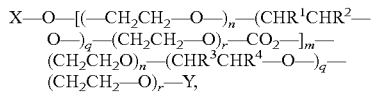

X—O—[(—$CH_2CH_2$—O—)$_n$—($CHR^1CHR^2$—O—)$_q$—($CH_2CH_2$—O)$_r$—$CO_2$—]$_m$—($CH_2CH_2O)_n$—($CHR^3CHR^4$—O—)$_q$—($CH_2CH_2$—O)$_r$—Y, wherein:
   n is an integer of from about 5 to about 500,
   q and r are integers each independently ranging from about 2 to about 2,000,
   m is an integer ranging from 1 to about 5,
   $R^1$, $R^2$, $R^3$, and $R^4$ are independently selected from alkyl or H, where
   $R^1$ is H when $R^2$ is alkyl or $R^1$ is alkyl when $R^2$ is H,
   $R^3$ is H when $R^4$ is alkyl or $R^3$ is alkyl when $R^4$ is H, and
   X and Y are each independently selected from the group consisting of H, alkyl, alkenyl and aryl, and
   (ii) a PEGylated antibody,
   in aqueous solution, wherein the polymer is not covalently crosslinked and is present at a concentration of from about 5% by weight to about 8% by weight, and the composition (i) is a liquid at ambient temperatures and (ii) forms a hydrolytically degradable gel at body temperature (37° C.).

2. The composition of claim 1, wherein X and Y are independently selected from H and alkyl.

3. The composition of claim 1, wherein n is an integer of from about 80 to about 120.

4. The composition of claim 1, wherein q is an integer of from about 40 to about 70.

5. The composition of claim 1, wherein r is an integer of from about 5 to about 100.

6. The composition of claim 1, wherein:
   $R^1$ is H when $R^2$ is methyl or ethyl, or $R^1$ is methyl or ethyl when $R^2$ is H; and
   $R^3$ is H when $R^4$ is methyl or ethyl, or $R^3$ is methyl or ethyl when $R^4$ is H.

7. The composition of claim 1, wherein n is an integer of from about 80 to about 120, q is an integer of from about 40 to about 70, r is an integer of from about 10 to about 50, and m is an integer of from 1 to about 5.

8. The composition of claim 1, wherein $R^1$ is H, $R^2$ is methyl, $R^3$ is H, and $R^4$ is methyl.

9. The composition of claim 1, wherein $R^1$ is H, $R^2$ is methyl, $R^3$ is H and $R^4$ is methyl.

10. The composition of claim 1, wherein the PEGylated antibody is a PEGylated Fab.

11. The composition of claim 1 in a form suitable for injection.

12. The composition of claim 1, in the form of a hydrogel.

* * * * *